United States Patent [19]
Øfjord et al.

[11] Patent Number: 5,972,641
[45] Date of Patent: Oct. 26, 1999

[54] RAPID COLIFORM DETECTION SYSTEM

[75] Inventors: Gro Øfjord, Hagan; Kari Skjånes; Nina Aalen, both of Oslo; James D. Berg, Jar, all of Norway

[73] Assignee: Colifast Systems ASA, Norway

[21] Appl. No.: 09/143,266

[22] Filed: Aug. 28, 1998

[51] Int. Cl.$^6$ .............................. C12Q 1/04; C12Q 1/02
[52] U.S. Cl. .............................. 435/34; 435/29; 435/14; 435/38; 435/41; 435/968
[58] Field of Search .................... 435/34, 29, 14, 435/38, 41, 968

[56] References Cited

U.S. PATENT DOCUMENTS

| | | | |
|---|---|---|---|
| 3,928,139 | 12/1975 | Dorn | 195/103.5 |
| 4,242,447 | 12/1980 | Findl et al. | 435/39 |
| 4,289,498 | 9/1981 | Baughman et al. | 23/230 |
| 4,340,671 | 7/1982 | Gibson | 435/32 |
| 4,587,213 | 5/1986 | Malecki | 435/39 |
| 4,591,554 | 5/1986 | Koumura et al. | 435/18 |
| 4,693,972 | 9/1987 | Mansour et al. | 435/34 |
| 4,777,137 | 10/1988 | Lemonnier | 435/299 |
| 4,923,804 | 5/1990 | Ley et al. | 435/38 |
| 4,925,789 | 5/1990 | Edberg | 435/38 |
| 5,292,644 | 3/1994 | Berg | 435/29 |
| 5,429,933 | 7/1995 | Edberg | 435/34 |
| 5,518,894 | 5/1996 | Berg | 435/34 |
| 5,541,082 | 7/1996 | Botchner | 435/34 |
| 5,550,032 | 8/1996 | Isbister | 435/39 |
| 5,610,029 | 3/1997 | Ehrenfeld et al. | 435/34 |
| 5,612,186 | 3/1997 | Huang et al. | 435/37 |
| 5,620,865 | 4/1997 | Chen et al. | 435/34 |
| 5,633,144 | 5/1997 | Bitton et al. | 435/38 |
| 5,663,057 | 9/1997 | Drocourt et al. | 435/40 |
| 5,726,031 | 3/1998 | Roth et al. | 435/34 |
| 5,780,259 | 7/1998 | Edberg | 435/34 |

FOREIGN PATENT DOCUMENTS

| | | |
|---|---|---|
| 8605206 | 9/1986 | WIPO. |
| 9614431 | 11/1995 | WIPO. |
| 9640980 | 5/1996 | WIPO. |
| 9718455 | 11/1996 | WIPO. |
| 9811252 | 9/1997 | WIPO. |

OTHER PUBLICATIONS

W.R. Bailey, E.G. Scott (1966) Staining Formulae and Procedures, Chapter 37, in *Diagnostic Microbiology*, Mosby Co., St. Louis, pp. 318–319.

Standard Methods for the Examination of Water and Wastewater, Seventeen Ed., 1989, American Public Health Association, Washington, D.C., pp. 9–80 to 9–97.

G.G. Geesey, (Nov. 1987) Survival of Microorganisms in Low Mutrient Waters, Chapter 1, in Biological Fouling of Industrial Waste Water Systems: A Problem Solving Approach, Water Micro Associates, California, M.W. Mittleman and G.G. Geesey eds., pp. 1–23.

"ColiQuik" Coliform Detection Method of Hach Chemical Co., pp. 112, 113, 119 of Hach Catalog.

"Colifast" Coliform Monitoring Method by Palintest (Brochure), p. 20., Feb. 1990.

B.H. Olson, D.L. Clark, B.B. Milner, M.H. Stewart, and R.L. Wolfe, "Total Coliform Detection in Drinking Water: Comparison of Membrane Filtration with Colilert and Coliquik", *Appl. Env. Micro.*, 57:1535–1539, May 1991.

S. Stratman, "Rapid Specific Environment Coliform Monitoring", *International Laboratory*, pp. 40–43, Dec. 1988.

"Research Applications: Proven Utility Benefits", *AWWA Research Foundation*, No. 4, May 1993.

Idexx Environmental Products Catalog, Idexx Laboratories, Inc. Westbrook, Maine, 1995, 4 pages.

Palintest Colilert Brochure, Palintest Ltd., England, 4 pages.

Colilert, The Breakthrough in Coliform and *E. coli* Testing, Brochure, Idexx Laboratories, Westbrook, Maine, Nov. 1993, 4 pages.

Snyder et al., "Pattern Recognition Analysis of In Vivo Enzyme–Substrate Fluorescence Velocities in Microorganism Detection and Identification", *Applied and Environmental Microbiology*, May 1986, pp. 969–977.

Maddocks et al., Technical Method. A Rapid Method For Identifying Bacterial Enzymes:, *The Journal of the Association of Clinical Pathologists*, 28(8):686, Aug. 1975.

*Primary Examiner*—Louise N. Leary
*Attorney, Agent, or Firm*—Dunlap, Codding & Rogers, P.C.

[57] ABSTRACT

A rapid method for detecting the presence or absence of coliform bacteria in a liquid or liquified dairy sample, for example skimmed milk. A growth medium containing a fluorogenic substrate is combined with the sample and is incubated for a brief period of about 7–9 hours after which a single fluorescence value is measured. Total or thermotolerant coliform bacteria are determined to be present in the sample if the single fluorescent measurement exceeds a predetermined threshold value.

32 Claims, No Drawings

RAPID COLIFORM DETECTION SYSTEM

CROSS REFERENCE TO RELATED APPLICATION

Not Applicable

STATEMENT REGARDING FEDERALLY SPONSORED RESEARCH OR DEVELOPMENT

Not Applicable

BACKGROUND

The present invention relates to rapid methods for detecting microorganisms in products for human consumption or use, and more particularly, but not by way of limitation, to rapid methods for detecting the presence or absence of total coliform bacteria, *E. coli* or thermotolerant coliform bacteria in milk products.

Protection from deleterious microbial contaminants is a global issue. Each year millions of people throughout the world become ill, and thousands die, from contaminated food and water. Disturbing newspaper headlines and stories of epidemic and endemic diseases have increased public awareness of these problems. Testing for bacteria has thus received increasing attention from consumers and public regulatory bodies. In view of this, there is a growing demand for faster methods of detecting microbial contamination. The constant media attention on severe health risks related to microbial contamination of products consumed by humans is leading to increased consumer awareness and public regulatory pressure regarding the safety and the quality of food, water and pharmaceutical products. In addition, economic forces are urging companies to reduce costs by reducing waste, processing time and stock levels.

Several incidents of food borne bacteria outbreaks have increased consumer awareness regarding the safety of and the exact contents of food products. Recent examples of microbial contamination receiving major public attention include:

The Japanese *E. coli* outbreak, May 1996. The severe outbreak of infections from the bacterium *E. coli* 0157:H7 in Osaka, Japan, caused the death of 8 and seriously sickened over 9,000. The source is believed to be radish sprouts from one single supplier.

The Scottish *E. coli* epidemic, 1996. The *E. coli* outbreak in Lanarshire, Scotland in 1996, created vast political turmoil and investigation after the deaths of 18 and hundreds affected from contaminated meat.

Norway, summer 1997: Alarmingly high numbers of *E. coli* bacterium (including a less aggressive type of the 0157 bacterium) was found in 800 tonnes meat from a Norwegian abattoir. This incident could have incurred large casualties.

Hudson Hamburger Contaminants, USA 1997. Twenty-five million pounds of hamburger meat were recalled and destroyed following the detection of pathogenic *E. coli* in samples of the meat.

It is estimated that the industrial market for detection of microbial contaminants was approximately 600 million tests in 1997, amounting to a value of approximately USD 2.5 billion. Of the tests performed annually, the food segment is by far the largest segment, with approximately 310 million tests (53%), followed by the pharmaceutical segment with approximately 200 million tests (32%), the beverage segment with approximately 60 million tests (10%) and finally the environmental segment with approximately 30 million tests (5%). More than 80% of today's testing is performed with slow traditional methods (giving results in 2–3 days), which are laborious and expensive to use. These methods typically use agar plates or standard pour plates (plastic dishes with a nutrient medium), enhancing bacterial growth so that they multiply and their presence can be identified visually as colonies and counted. It is expected that the need for more effective measurements will lead to a significant conversion from slower traditional methods to more rapid and easy to use methods over the next 5 to 10 years. The total market is expected to exceed 800 million tests by 2005, and it is believed that rapid methods will represent 30–40% of the market.

Traditional microbiological methods, which take 18–72 hours to generate results, have led existing regulations to focus on testing of finished products. However, sampling from end product batches for testing does not guarantee that all products in one batch are of good quality. Food processing involves a number of steps and hand-overs (e.g. from the abattoir to the fast food restaurant), giving multiple operations and points for potential microbial carry-over and contamination. The nature of end product testing can therefore not capture every incident of microbial contamination. The ability to rapidly test for contamination at various steps early in a production line would minimize the chances that entire batches of products would have to be destroyed, as is often the case when only end point testing is carried out.

However, with the demand for "just-in-time" deliveries, few companies are able to wait for results of microbial testing. Traditional test methods therefore have value only for historical and documentation purposes. Some producers, however, hold goods until test results are complete, thus raising stock costs. The ability to provide "real time" information for the factories, avoiding contaminated products being shipped, reducing wastage and stocks is therefore desired.

Manufacturers who fail to deliver safe and high quality food products face severe problems, like reduced brand name value, loss or sales, product liability suits and, in worst case, plant closures. The retail industry has increasingly adopted private labels in shelves. The risk of bad publicity and loss of sales in case of "food poisoning" from their branded products, leads retailers to request documentation or testing and implementation of microbial quality control systems from their suppliers. This puts pressure for increased quality control throughout the entire product chain, from delivery of raw materials, through processing, to the end-products.

Over the last 20 years, some new and "easy to use" methods (such as COLILERT and 3M PETRIFILM) have been introduced and have gained approximately 15% of the total market today. These methods are different from the traditional methods in that they have made daily laboratory work easier by reducing many of the practical steps operators take when conducting microbial tests. However, the detection time for these methods, although down from 2–3 days, is still about one day. This is still too long for products that are finished and already shipped to customers. These new tests have therefore not significantly altered how and where companies perform their routine tests.

COLILERT is a 24 hour growth-based method for detection of coliforms/*E. coli* in drinking water. The product has gained widespread usage in the U.S. PETRIFILM, by 3M, represents another product targeted at making microbiology measurements easier to do for workers. Petrifilm is similar to traditional methods regarding time to results and reading of results but eliminates or minimizes sample and media preparations. This is an advance and makes results much more consistent.

Also, in the last 3–4 years, a new class of rapid tests for microbial contamination has managed to gain a market share of approximately 5%, amounting to 30 million tests. Food processing plants must routinely stop production to clean and sanitize the facility. In many plants this occurs during the night, before the plant begins production in the morning. Plant quality control analysts have been perplexed about how to determine if the plant is properly sanitized.

An effective HACCP (Hazard Analysis Critical Control Point) program is dependent upon access to rapid and easy-to-use sanitation screening tests, especially in early states in the production process.

Healthy animals carry pathogens for humans in their intestines and on their hide and hooves. Slaughter unavoidably disseminates these pathogens to the carcass. Excision is considered the most effective bacterial sampling method, but in red meat processing facilities excision is neither practical nor acceptable. Consequently a more practical, non-destructive, and rapid method for carcass bacterial sampling must be validated. These factors should be accomplished without significantly affecting the total sum of recovered bacteria.

Traditional methods for assaying bacteria on surfaces are based on swabbing the surface followed by either a culture of the swab in a media that supports growth or by rinsing swab in a buffer and plate on agar and incubation for 24–48 hours. Other methods are to use contact plates or petrifilm to press on the surface, and then incubate for 24 to 72 hours. (The disadvantage with the contact plates and petrifilm is that they cannot be used on wet surfaces, and they may leave some of the growth medium on the carcass, enhancing bacterial growth).

To satisfy this need rapid (5 minutes) tests measuring ATP (adenosine triphosphate), a biological molecule which is present in among all living microorganisms, have been developed. The test can determine whether a facility has been properly cleaned and sanitized. It is also a very easy to use test, so it can be incorporated into the job of the cleaning crew and does not have to be performed by laboratory technicians. However, the ATP test does not specifically detect bacterial contamination, only the presence of organic materials which contain ATP.

The purpose of microbial testing is mainly to identify the presence and risk of presence of bacteria dangerous to the human body. In many cases the level of contamination must also be measured, and in certain cases the microbes must be identified. Microbial tests typically cover either one specific bacterium, or a limited spectrum of bacteria. They are also often limited to testing of specific substances (e.g. water, meat, surfaces).

Specific pathogens are difficult and time-consuming to detect, often taking several days. Hence, indicators of the presence of pathogens, such as coliforms are preferred for analysis and monitoring of water and food quality.

Indicator testing for Total Viable Organisms (referred to TVO or TVC) and coliforms are the most widely used tests for routine monitoring of microbial contamination. Microbial testing and technology requirements vary widely across industries.

The environmental industry segment is concerned with the monitoring of water quality in drinking water, and bathing water (e.g., spas and swimming pools) manufacturing process water, and ambient/recreational water. The global market consists of approximately 30 million tests, mainly for coliforms/*E. coli* in drinking water. Routine testing of drinking water has traditionally been enforced by stringent public regulatory requirements in every country.

The non-alcoholic beverage industry consists of the bottled water, stilled soft drinks, carbonated soft drinks, and beer production segments. The majority of coliform tests in the beverage industry are performed on bottled water. Larger bottled water producers acknowledge that more rapid results would help them reduce stock levels and potential costs related to calling back shipped products.

The food processing industry consists of a number of products, including milk and dairy products, meat, fish agriculture and multiple food manufacturing products, with different regulatory and company requirements for microbial testing. The industry currently demands a range of technologies to accommodate its testing needs, comply with new regulations, enhance food safety and reduce costs associated with laboratory testing, processing times and stock levels.

Standard testing procedures in the milk industry currently include the following:

(1) International Dairy Federation (IDF) 73A:1985, Milk and Milk Products, Enumeration of coliforms—colony count technique and most probable number at 30° C.;

(2) International Standard, ISO, 5541/1 Milk and milk products, Enumeration of coliforms—Part 1: Colony count technique and most probable number at 30° C. First ed. Dec. 1, 1986;

(3) International Standard, ISO, 5541/2 Milk and milk products, Enumeration of coliforms—Part 2: Most probable number at 30° C. First ed. Dec. 1, 1986; and (4) International Standard, ISO, 11866/3 Milk and milk products, Enumeration presumptive *Escherichia coli*—Part 3: Colony count technique at 44° C. using membranes. First ed. Feb. 15, 1997.

Unfortunately, these methods generally take at least 48 to 72 hours to obtain results.

The pharmaceutical industry performs approximately 200 million tests annually and requires the highest standard of microbial quality. Pharmaceutical producers are seeking better control of incoming raw materials, processing stages and final products.

The food service industry (such as caterers and fast food restaurants) is pushing suppliers to document quality of delivered products. Today routine bacteria tests are mostly performed at external laboratories. However, there is reason to believe that recent severe incidents of microbial contamination, leading to food-borne disease outbreaks and fatalities have lead the food service industry to reevaluate its quality assurance systems. It is believed that giving caterers the possibility of near-real-time test for specific bacteria indicators like coliforms (as opposed general tests which detect ATP), in the form of a simple instrument test would help companies secure the quality of their sanitation process and incoming products.

As evident from the above, there continues to be a need for methods which will rapidly detect the presence of total coliform bacteria, thermotolerant (including fecal) coliform bacteria or *E. coli* or pathogenic *E. coli* 0–157 in samples.

SUMMARY OF THE INVENTION

In a preferred embodiment, the present invention comprises a direct addition method for rapidly determining the presence or absence of coliform bacteria in a liquid milk sample. In this version of the invention, a sample of milk (e.g. skimmed milk, lowfat milk, whole milk, or cream) is combined directly with a quantity of growth medium. The sample is not filtered. After a predetermined incubation period, a single fluorescence measurement of the particular sample is taken.

The fluorescence measurement is used to determine the concentration of a fluorogenic product (e.g., 4-methylumbelliferone) in the sample. The amount of the fluorogenic product is related to the number of total or fecal coliform cells in the sample. If the concentration of the fluorogenic product equals or exceeds a predetermined threshold level, it is determined that total or thermotolerant coliform bacteria are present in the sample (depending on the choice of incubation temperature). If the concentration of the fluorogenic product is less than the predetermined threshold level, it is determined that total or thermotolerant coliform bacteria are absent from the sample, based on a predetermined definition of presence and absence.

DESCRIPTION OF THE PREFERRED EMBODIMENTS

The present invention comprises rapid methods of detecting bacterial contamination of various liquid and solid food products, in particular, milk products, and areas used to prepare or process such items, wherein the food product or sample from the work area or surface, is preferably directly added to a growth medium having a fluorogenic substrate, then incubated, then evaluated for a fluorescence emission from a fluorogenic product.

The methods described herein rely upon the enzymatic hydrolysis by coliform bacteria of one or both of two fluorogenic substrates (4-methylumbelliferone-β-D-galactoside and/or 4-methylumbelliferone-β-D-glucuronide) which yields a product (4-methylumbelliferone) which fluoresces upon exposure to an excitation wavelength of light. The fluorescence emission can be quantified using a standard fluorometer.

In practice, samples are incubated at a preferred temperature, which is about 39° C.±5° C. for about 9 hours to determine presence of total coliforms, about 44.0° C.±0.5° C. for 7–9 hours to determine presence of fecal coliform cells, about 42° C. for pathogenic E. coli cells or in another embodiment, about 30° C. for 11–12 hours for determining total coliforms. "Total coliform" bacteria are those coliform bacteria which are normally present in the colon or small intestine of humans or animals. "Thermotolerant coliform" bacteria include those coliform bacteria which are generally present in the feces of humans or animals and/or which are tolerant of high incubation temperatures. Both of these groups are used as indicators of sanitary quality. The samples are removed after predetermined incubation times for either pass/fail or presence-absence results. Presence of coliform bacteria in a water sample, for example, is defined as at least one coliform cell per 100 milliliters. Presence of coliform bacteria in a dairy product, e.g., milk, is defined herein as at least one coliform cell per 1 milliliter. The sample is incubated using an incubator which has a heat transference medium which maintains an intimate physical contact with each container. Examples of such heat transference media are water, oil, and metal, or other conductive solids.

For example, in one embodiment the invention contemplates a rapid method for determining presence or absence of coliforms in an original unfiltered liquid or liquified sample, e.g. skim milk, comprising:

(a) combining the original sample with an actuating medium having a fat emulsifying composition and a fluorogenic substrate which when metabolized yields a fluorescent product, preferably 4-methylumbelliferone;

(b) incubating the combined sample and actuating medium mixture at a temperature preferred for incubating total, thermotolerant, or E. coli coliform cells, for a predetermined duration;

(c) adjusting the pH of the incubated combined sample to an alkaline pH and irradiating said sample with a predetermined excitation wavelength of light;

(d) measuring a fluorescence value from the irradiated combined sample; and (e) concluding that the original sample is contaminated with the specified bacteria when the fluorescence value equals or exceeds a predetermined threshold value which corresponds to a particular concentration value of the fluorescent product.

In the present invention, the actuating medium comprises a nutrient for supporting metabolism of the live total coliform, thermotolerant coliform, or E. coli cells, an induction agent for inducing an enzyme effective in reacting with the substrate for producing the fluorogenic product, and in one embodiment, a surfactant effective in enhancing fluorescence or its production and in another embodiment, bile salts for inhibiting gram positive bacteria and for emulsifying fat in milk products. The induction agent may be lactose or IPTG, for example, the surfactant effective in enhancing fluorescence may be sodium lauryl sulfate or tergitol, the enzyme may be β-D-galactosidase or β-D-glucuronidase, the fluorogenic substrate may be 4-methylumbelliferone-β-D-galactoside and/or 4-methylumbelliferone-β-D-glucuronide, the latter which uses β-D-glucuronidase as the enzyme for degrading the substrate to 4-methylumbelliferone, and the fluorescent product may be 4-methylumbelliferone. Preferably, the irradiation step uses an excitation wavelength of about 380 nm which causes an emission wavelength of about 450 nm from the fluorescent product. When the pH of the incubated sample is adjusted, the adjustment may be made using NaOH, for example, to a pH of above 9 or more preferably, to a pH of above 11, or above 13.

In all versions of the present invention, the culture medium used in determining if an original liquid or liquified sample is contaminated may comprise an aqueous or dry mixture, 4-methylumbelliferone-β-D-galactoside and/or 4-methylumbelliferone-β-D-glucuronide and growth actuators.

In one embodiment, the composition of the actuating (culture) medium for mixing with water or liquid sample may comprise in dry form about 20% to about 25% by weight of a peptone, about 10% to 15% by weight of a yeast extract, about 0.2% to 2% by weight of an enzyme inducer, about 20% to 40% by weight of a salt for maintaining isotonicity, about 20% to 25% by weight of pyruvate, about 0.5% to 10% by weight of bile salts, and optimally, about 0.5% to 4.0% by weight of another detergent. The peptone may be proteose peptone No. 3, for example, the salt may be NaCl and the detergent may be sodium lauryl sulfate or tergitol. As noted above, the medium may further comprise 4-methylumbelliferone-β-D-galactoside and/or 4-methylumbelliferone-β-D-glucuronide as fluorogenic substrates, and the fluorogenic substrates may comprise about 0.1% to 2% by weight of the medium.

It will be understood that any actuating medium is suitable as long as the medium functions in accordance with the present invention.

More particularly, the present invention comprises a method for evaluating the presence or absence of coliform bacteria in a milk or liquid dairy sample. The method may comprise the steps of (1) providing an original milk sample, (2) forming an incubation mixture by combining the milk sample with a culture medium comprising a fluorogenic substrate capable of being acted on by coliform bacteria to form a detectable fluorogenic product, (3) incubating the incubation mixture at an incubation temperature for a period of from about 7 to about 9 hours, (4) irradiating the incubated combined sample with an excitation wavelength and measuring the fluorescence emitted from the incubated combined sample and determining a concentration of the fluorogenic product in the incubated sample, and (5) concluding that coliform bacteria were present in the original sample when the concentration of the fluorogenic product in the sample equals or exceeds 8 parts per billion or concluding that coliform bacteria were absent in the original sample when the concentration of the fluorogenic product is less than 8 parts per billion. In this method the incubation period is preferably about 9 hours, and the incubation temperature is preferably about 39° C.±0.5° C., wherein the presence or absence of total coliforms is detected. Alternatively, the incubation temperature is about 44° C.±0.5° C., the incubation period is 7–9 hours, wherein the method detects the presence or absence of thermotolerant coliform bacteria. In the method the milk sample may be skimmed milk, lowfat milk, whole milk, or cream. The excitation wavelength is preferably about 380 nm and the emission wavelength is about 450 nm. Alternatively, the sample may be irradiated with any excitation wavelength which is effective in causing fluorescence in accordance with the present invention. The culture medium contains a fat emulsifier, which preferably comprises bile salts. In this method, the milk sample is not filtered prior to incubation. The fluorogenic product is preferably 4-methylumbelliferone and the fluorogenic substrates comprise at least one of 4-methylumbelliferone-β-D-galactoside and 4-methylumbelliferone-β-D-glucuronide.

More particularly, the method is a method for evaluating the presence or absence of total coliform bacteria in a milk sample, comprising the steps of (1) providing an original milk sample, (2) forming an incubation mixture by combining the milk sample with a culture medium comprising a fluorogenic substrate capable of being acted on by coliform bacteria to form a detectable fluorogenic product, (3) incubating the incubation mixture at an incubation temperature of about 39° C.±0.5° C. for a period of about 9 hours, (4) irradiating the incubated incubation mixture with an excitation wavelength and measuring the fluorescence emitted from the incubated incubation mixture and determining a concentration of the fluorogenic product therein, and (5) concluding that total coliform bacteria were present in the original milk sample when the concentration of the fluorogenic product equals or exceeds 8 parts per billion and concluding that total coliform bacteria were absent in the original sample when the concentration of the fluorogenic product is less than 8 parts per billion. As above, the milk sample may be skimmed milk, lowfat milk, whole milk, or cream. The culture medium contains a fat emulsifier, preferably comprising bile salts. The fluorogenic product is preferably 4-methylumbelliferone, and the fluorogenic substrate is at least one of 4-methylumbelliferone-β-D-galactoside and 4-methylumbelliferone-β-D-glucuronide.

In another embodiment, the invention comprises a method for evaluating the presence or absence of thermotolerant coliform bacteria in a milk or liquid dairy sample, comprising the steps of (1) providing an original milk sample, (2) forming an incubation mixture by combining the milk sample with a culture medium comprising a fluorogenic substrate capable of being acted on by coliform bacteria to form a detectable fluorogenic product, (3) incubating the incubation mixture at an incubation temperature of about 44° C.±0.5° C. for a period of from about 7 to about 9 hours, (4) irradiating the incubated incubation mixture with an excitation wavelength and measuring the fluorescence emitted from the incubated incubation mixture and determining a concentration of the fluorogenic product therein, and (5) concluding that thermotolerant coliform bacteria were present in the original milk sample when the concentration of the fluorogenic product equals or exceeds 8 parts per billion and concluding that thermotolerant coliform bacteria were absent in the original sample when the concentration of the fluorogenic product is less than 8 parts per billion. More particularly, the incubation period is about 7 hours or is about 8 hours. The milk sample may be lowfat milk, whole milk, skimmed milk, or cream. The culture medium contains a fat emulsifier, which may comprise bile salts. The milk sample is not filtered prior to incubation. The fluorogenic product is preferably 4-methylumbelliferone, and the fluorogenic substrate is at least one of 4-methylumbelliferone-β-D-galactoside and 4-methylumbelliferone-β-D-glucuronide.

EXAMPLES

The following examples are intended to further illustrate methods of the present invention including preferred versions; however, these examples are not to be construed as limitations of this invention.

Example 1

Direct Addition-Liquid Samples. In this method a 100 ml sample of a liquid is directly combined with a quantity of the growth medium containing 4-methylumbelliferone-β-D-glucuronide or 4-methylumbelliferone-β-D-galactoside for incubation. A duplicate sample is prepared as a control and a fluorescence measurement is taken thereof. No filtering step is used in this process.

The incubation sample is incubated as described elsewhere herein for a predetermined time depending upon the specific bacterial contaminant (total coliforms, thermotolerant coliforms, or pathogenic *E. coli*) which is desired to be detected. After the predetermined incubation time, the sample is removed from the incubator, and an alkalizing agent is added to the sample to increase the pH to an alkaline pH for improving the fluorescence detectability of the sample. After adjusting the pH of the incubated sample, the sample is irradiated with a predetermined excitation wavelength of light as discussed elsewhere herein. A fluorescence measurement is then taken of the incubated sample and is corrected using the fluorescence measurement taken from the non-incubated control sample. Depending on the identity of the sample tested, a presence/absence or pass/fail decision can be made regarding coliform contamination of the original sample.

For example, if the sample is raw, ambient, or bottled water, a net positive fluorescence determination taken from a sample incubated for six hours indicates the presence of a particular category of microorganism, such as coliform bacteria, depending on the incubation temperature and media components, as discussed elsewhere herein. A net negative fluorescence determination indicates the absence of said microorganism. In another embodiment, a net positive fluorescence determination taken from a sample incubated for 1 hour would, for example, indicate the presence above a predetermined threshold of bacteria of a particular category, depending on the incubation temperature and media. Examples of the types of substances which may be tested using this method are water, beverages (tea, soft drinks, juices), and urine.

Example 2

Direct Addition-Milk Products

In a preferred embodiment of this method, a sample of milk (skimmed, lowfat, whole or cream) and a quantity of growth medium are combined in a 3:1 ratio. The specific ingredients of the preferred medium used herein are shown in Table 2 (dry weights). The added medium may be liquified as prepared as shown for the medium in Table 1 or it may be added directly as dry medium to the milk and mixed.

In a preferred version, 3 ml of milk and 1 ml of medium are mixed and disposed in a 4.5 ml cuvette. The sample is then incubated at about 39° C. In alternative embodiments the total mixture may be 10 ml (7.5 ml of milk: 2.5 ml of medium) or 80 ml (60 ml of milk: 20 ml of medium).

After an incubation period of at least about 9 hours, the sample is treated with an alkalizing agent as discussed elsewhere herein and irradiated with an excitation wavelength. A fluorescence measurement is then recorded. If the fluorescence measurement indicates that the sample has a 4-methylumbelliferone (MU) concentration equal to or in excess of about 8 $\mu g/l$ (8 ppb), the sample is considered to be positive for the presence of coliforms. If the MU concentration is below about 8 $\mu g/l$ (8 ppb), the sample is considered to be negative for the presence of coliforms. In this embodiment, the milk may have a fat content of from about 0.1% (skim) to about 38% (cream). Other milk products with fat contents within this range are also contemplated by the present invention. Presence of coliforms is defined as being 1 cfu/1 ml.

In a preferred version of the method, the medium comprises a fat emulsifier for dispersing the fat in the milk sample to a sufficient degree to enable growth of coliform bacteria associated with the fat globules in the sample. In an especially preferred version the fat emulsifier comprises bile salts.

Example 3

Methods

The following methods and compositions may be used as indicated in the various embodiments of the present invention represented herein.

Filtration

Where a filtering step is used in the method, the sample is filtered in accordance with the membrane filtration procedure published in Section 9222D, of *Standard Methods For the Examination of Waste and Wastewater*, 17th Ed., American Public Health Association, 1989, which is hereby incorporated herein by reference.

Use of Fluorometer In one embodiment, a Turner Designs TD-700 fluorometer is used using the following procedures:

Calibration

Calibration should be performed every day. Use the Multi-Optional mode calibration procedures.

Transfer 4 ml of HC solution into square cuvette. Cap vial with parafilm and put it in the water bath for 5–10 minutes. Calibration solution should always be heated to test temperature (e.g. 44.5° C. for FC-test) before calibration.

| The TD-700 display shows: | 1. Setup |
|---|---|
| | 2. Calibration |
| If not press <ESC> twice. | |

Press <2> from the setup/cal screen. Take the HC vial out from the water bath. Dry outside of the vial, moisture on the outside will result in error. Add 100 $\mu l$ 2.5 M NaOH. Cover opening with parafilm and invert vial 3 times. NBI The time from when NaOH is added until the sample is placed in the reading cell, should not exceed 20 seconds. Insert vial into the sample adaptor in the sample chamber. Accept the default value of 800 by pressing <1>. When the sample is set, the TD-700 asks if you want to run a blank. Press <9> for not withdrawing a blank. the calibration is done and measurements can start. Run a HC to check if the rfu is around 800. Also run HC samples during a day to control if there is a drift in the instrument.

Reading Samples

Take out 4 ml sample or take out cuvette from incubator. Add 100 $\mu l$ 2.5 M NaOH. Cover opening with parafilm and invert vial 3 times, and read sample as described above.

If the TD-700 starts to countdown from 600 during an experiment just hit the <ESC> button.

It will be understood that other fluorometers made be employed in the present method.

In the preferred embodiment, the incubator comprises a metal block with cavities for the sample vials. However, the incubator can be any apparatus, such as a water bath, which can maintain a stable incubating temperature and which has a heat transference medium which maintains an intimate physical contact with the container surface. This includes incubators with liquid media such as water or oil, and block or sink incubators having a solid or metal heat transference medium.

Equipment and Supplies

Equipment and supplies used in the pass/fail or presence-absence tests may include a membrane filtration apparatus, a water bath incubator able to hold a temperature constant about the preferred incubation temperature, actuating media, dilution water (e.g., 0.1% sterile peptone or phosphate buffer), membrane filters (e.g., 0.45 $\mu m$ with grid), 4-methylumbelliferone-β-D-galactoside (MUGal), sodium lauryl sulfate, tergitol, a fluorometer, a solution of 2.5 M NaOH, sterile incubation tubes, square cuvettes (e.g. 4.5 ml PMMA) and 4-methylumbelliferone (4-MU).

Preparation of Liquid Actuating Media

Rehydrate 21 g of an actuating media (examples of compositions shown in Table 1 and Table 2) in 300 ml of cold water. Add 700 ml of boiling water and stir.

TABLE 1

Actuating Media Composition

| Ingredient | Dry Weight (gm.) |
|---|---|
| Proteose peptone no. 3 | 100 |
| Yeast extract | 60 |
| IPTG | 2 |
| NaCl | 150 |
| Pyruvate | 100 |
| Sodium lauryl sulphate or Tergitol | 4 |
| Bile salts | 2 |

TABLE 1-continued

Actuating Media Composition

| Ingredient | Dry Weight (gm.) |
| --- | --- |
| 4-methylumbelliferone-β-D-galactoside | 1 gm |
| 4-methylumbelliferone-β-D-glucuronide | 1 gm |
| | total 420 gm |

TABLE 2

Alternate Actuating Medium Composition

| Ingredients | Dry Weight (gm.) |
| --- | --- |
| Proteose peptone no. 3 | 100 |
| Yeast extract | 60 |
| IPTG | 8 |
| NaCl | 150 |
| Pyruvate | 100 |
| SLS or tergitol | 16 |
| Bile salts | 40 |
| 4-methylumbelliferone-β-D-galactoside | 4 |
| 4-methylumbelliferone-β-D-glucuronide | 4 |

Preparation of Internal Calibration Standard

First prepare a 68.1 μM MU stock solution by dissolving 6 mg of 4-MU in 500 ml of media without MU4-methylumbelliferone-β-D-galactoside. Prepare fresh stock solution each second week. Dilute 1 ml of the stock solution to 250 ml with media to prepare a Working solution (0.27 μM MU). This is used as the calibration standard. Fresh working solution is preferably prepared each week.

All patents or publications cited herein are hereby incorporated herein by reference.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method for evaluating the presence or absence of total coliform bacteria in a milk or liquid dairy sample, comprising:
   providing an original milk sample;
   forming an incubation mixture by combining the milk sample with a culture medium comprising a fluorogenic substrate capable of being acted on by coliform bacteria to form a detectable fluorogenic product;
   incubating the incubation mixture at a predetermined incubation temperature for an incubation period of from about 7 to about 9 hours;
   irradiating the incubated combined sample with an excitation wavelength and measuring the fluorescence emitted from the incubated combined sample and determining a concentration of the fluorogenic product in the incubated sample; and
   concluding that coliform bacteria were present in the original sample when the concentration of the fluorogenic product in the sample equals or exceeds 8 parts per billion and concluding that coliform bacteria were absent in the original sample when the concentration of the fluorogenic product is less than about 8 parts per billion.

2. The method of claim 1 wherein the incubation period is about 9 hours.

3. The method of claim 2 wherein the predetermined incubation temperature is about 39° C.±0.5° C.

4. The method of claim 3 wherein the method detects the presence or absence of total coliforms.

5. The method of claim 1 wherein the predetermined incubation temperature is about 44° C.±0.5° C.

6. The method of claim 5 wherein the method detects the presence or absence of thermotolerant coliform bacteria.

7. The method of claim 1 wherein the incubation is 7–9 hours and the predetermined incubation temperature period is 39° C.±0.5° C. and the method detects the presence or absence of total coliform bacteria.

8. The method of claim 1 wherein the milk sample is selected from the group comprising skimmed milk, lowfat milk, whole milk and cream.

9. The method of claim 1 wherein the excitation wavelength is about 380 nm and the emission wavelength is about 450 nm.

10. The method of claim 1 wherein the culture medium contains a fat emulsifier.

11. The method of claim 10 wherein the fat emulsifier comprises bile salts.

12. The method of claim 1 wherein the milk sample is not filtered prior to incubation.

13. The method of claim 1 wherein the fluorogenic product is 4-methylumbelliferone.

14. The method of claim 1 wherein the substrate is at least one of 4-methylumbelliferone-β-D-galactoside and 4-methylumbelliferone-β-D-glucuronide.

15. A method for evaluating the presence or absence of total coliform bacteria in a milk sample, comprising:
   providing an original milk sample;
   forming an incubation mixture by combining the milk sample with a culture medium comprising a fluorogenic substrate capable of being acted on by coliform bacteria to form a methylumbelliferone;
   incubating the incubation mixture at an incubation temperature of about 39° C.±0.5° C. for a period of about 9 hours;
   irradiating the incubated incubation mixture with an excitation wavelength and measuring the fluorescence emitted from the incubated incubation mixture and determining a methylumbelliferone concentration therein; and
   concluding that total coliform bacteria were present in the original milk sample when the methylumbelliferone concentration equals or exceeds 8 parts per billion and concluding that total coliform bacteria were absent in the original sample when the methylumbelliferone concentration is less than 8 parts per billion.

16. The method of claim 15 wherein the milk sample is selected from the group comprising skimmed milk, lowfat milk, whole milk and cream.

17. The method of claim 15 wherein the excitation wavelength is about 380 nm and the emission wavelength is about 450 nm.

18. The method of claim 15 wherein the culture medium contains a fat emulsifier.

19. The method of claim 18 wherein the fat emulsifier comprises bile salts.

20. The method of claim 15 wherein the milk sample is not filtered prior to incubation.

21. The method of claim 15 wherein the methylumbelliferone is 4-methylumbelliferone.

22. The method of claim 15 wherein the fluorogenic substrate is at least one of 4-methylumbelliferone-β-D-galactoside and 4-methylumbelliferone-β-D-glucuronide.

23. A method for evaluating the presence or absence of thermotolerant coliform bacteria in a milk or liquid dairy sample, comprising:

provinding an original milk sample;

forming an incubation mixture by combining the milk sample with a culture medium comprising a fluorogenic substrate capable of being acted on by coliform bacteria to form methylumbelliferone;

incubating the incubation mixture at an incubation temperature of about 44° C.±0.5° C. for a period of from about 7 to about 9 hours;

irradiating the incubated incubation mixture with an excitation wavelength and measuring the fluorescence emitted from the incubated incubation mixture and determining a methylumbelliferone concentration therein; and concluding that thermotolerant coliform bacteria were present in the original milk sample when the methylumbelliferone concentration equals or exceeds 8 parts per billion and concluding that thermotolerant coliform bacteria were absent in the original sample when the methylumbelliferone concentration is less than 8 parts per billion.

24. The method of claim 23 wherein the predetermined incubation period is about 7 hours.

25. The method of claim 23 wherein the predetermined incubation period is about 8 hours.

26. The method of claim 23 wherein the excitation wavelength is about 380 nm and the emission wavelength is about 450 nm.

27. The method of claim 23 wherein the milk sample is skimmed milk, lowfat milk, whole milk and cream.

28. The method of claim 23 wherein the culture medium contains a fat emulsifier.

29. The method of claim 28 wherein the fat emulsifier comprises bile salts.

30. The method of claim 23 wherein the milk sample is not filtered prior to incubation.

31. The method of claim 23 wherein the methylumbelliferone is 4-methylumbelliferone.

32. The method of claim 23 wherein the fluorogenic substrate is at least one of 4-methylumbelliferone-β-D-galactoside and 4-methylumbelliferone-β-D-glucuronide.

* * * * *